United States Patent [19]
Shannon et al.

[11] Patent Number: 6,063,817
[45] Date of Patent: May 16, 2000

[54] USE OF SUBSTITUTED (5,6) DIHYDRONAPHTHALENYL COMPOUNDS HAVING RETINOID-LIKE ACTIVITY TO PREVENT OR REDUCE ISCHEMIC INJURY

[75] Inventors: Ronald J. Shannon, Washington Crossing, Pa.; Karyn A. Monte, Hightstown, N.J.; Kenneth Tramposch, E. Amherst, N.Y.

[73] Assignee: Bristol-Myers Squibb Company, New York, N.Y.

[21] Appl. No.: 09/026,404

[22] Filed: Feb. 19, 1998

Related U.S. Application Data

[60] Provisional application No. 60/038,302, Feb. 21, 1997.
[51] Int. Cl.[7] .................................................. A61K 31/00
[52] U.S. Cl. ........................ 514/617; 514/619; 514/533; 514/513; 514/561; 514/562; 514/563; 514/569; 514/887; 514/928
[58] Field of Search .................................... 514/513, 561, 514/562, 563, 569, 887, 928, 617, 619, 533

[56] References Cited

U.S. PATENT DOCUMENTS

| | | | |
|---|---|---|---|
| 3,689,667 | 9/1972 | Lee | 424/318 |
| 3,729,568 | 4/1973 | Kligman | 424/318 |
| 3,856,934 | 12/1974 | Kligman | 424/62 |
| 3,882,244 | 5/1975 | Lee | 424/318 |
| 3,896,789 | 7/1975 | Trancik | 128/2 |
| 3,906,108 | 9/1975 | Felty | 424/318 |
| 3,932,665 | 1/1976 | Van Scott et al. | 424/333 |
| 3,966,967 | 6/1976 | Lee | 424/318 |
| 4,048,204 | 9/1977 | Lee | 260/413 |
| 4,055,659 | 10/1977 | Gander et al. | 424/305 |
| 4,126,693 | 11/1978 | Gander et al. | 424/282 |
| 4,126,697 | 11/1978 | Gander et al. | 424/305 |
| 4,126,698 | 11/1978 | Gander et al. | 424/305 |
| 4,126,699 | 11/1978 | Gander et al. | 424/305 |
| 4,129,662 | 12/1978 | Gander et al. | 424/305 |
| 4,211,782 | 7/1980 | Vane et al. | 424/263 |
| 4,214,000 | 7/1980 | Papa | 424/289 |
| 4,304,787 | 12/1981 | Gander et al. | 424/305 |
| 4,487,782 | 12/1984 | Mezick | 424/317 |
| 4,538,603 | 9/1985 | Pawelchak et al. | 128/156 |
| 4,551,490 | 11/1985 | Doyle et al. | 525/22 |
| 4,677,120 | 6/1987 | Parish et al. | 514/549 |
| 4,727,088 | 2/1988 | Scott et al. | 514/725 |
| 4,757,140 | 7/1988 | DeLuca et al. | 536/27 |
| 4,889,847 | 12/1989 | Kligman et al. | 514/171 |
| 5,059,189 | 10/1991 | Cliento et al. | 604/307 |
| 5,648,385 | 7/1997 | Starrett, Jr. et al. | 514/513 |

FOREIGN PATENT DOCUMENTS

| | | |
|---|---|---|
| 0253393 | 1/1988 | European Pat. Off. . |
| 0266992 | 5/1988 | European Pat. Off. . |
| 0307187 | 3/1989 | European Pat. Off. . |
| 0370789 | 5/1990 | European Pat. Off. . |
| 0448213 | 2/1991 | European Pat. Off. . |
| 0661259 | 7/1995 | European Pat. Off. . |

OTHER PUBLICATIONS

Shea. Pressure Sores. Clin. Orthopaedics & Related Research. 1975, No. 112, pp. 89–100.

Smith et al. Causes of venous ulceration: a new hypothesis. British Medical Journal, vol. 296, Jun. 18, 1988, pp. 1726–1727.

(List continued on next page.)

*Primary Examiner*—Dwayne C. Jones
*Assistant Examiner*—C. Delacroix-Muirheid
*Attorney, Agent, or Firm*—John M. Kilcoyne; Theodore R. Furman, Jr.

[57] ABSTRACT

The present invention relates to methods of preventing, or reducing the severity of, an ischemic injury originating in an animal's dermal tissue by applying to the animal a composition comprising a compound of formula I*:

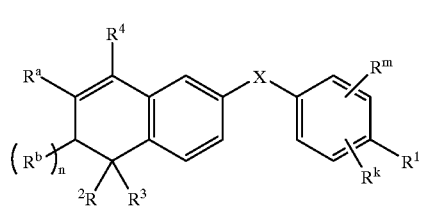

I* or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —CH=CH—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

n is 1 or 0;

R$^m$ and R$^k$ are independently hydrogen, halogen, C$_{1-6}$ alkyl, hydroxy, C$_{1-6}$ alkyloxy or nitro;

R$^4$ is —(CH$_2$)$_t$—Y$^b$, C$_{1-6}$ alkyl, or C$_{3-6}$ cycloalkyl;

R$^1$ is —CO$_2$Z, C$_{1-6}$ alkyl, CH$_2$OH, —CONHR$^y$, or CHO;

R$^a$ and R$^b$ are independently hydrogen or C$_{1-6}$ alkyl, or R$^a$ and R$^b$ together can form a radical of the formula: Arch Dermatol, vol. 125, Jan. 1989, pp. 65–69.

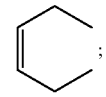

Y$^b$ is naphthyl or phenyl, both radicals can be optionally substituted with one to three of C$_{1-6}$ alkyl or halogen, which substituents can be the same or different;

Z is hydrogen or C$_{1-6}$ alkyl;

R$^2$, R$^3$, R$^5$, R$^6$, and R$^y$ are independently hydrogen or C$_{1-6}$ alkyl; and t is zero to six.

21 Claims, No Drawings

OTHER PUBLICATIONS

Kligman. Preventing, Delaying, and Repairing Photoaged Skin. Cutis, 41: 419–420, 1988.

Bryce et al. Retinoic Acids Promote the Repair of the Dermal Damage and the Effacement of Wrinkles in the UVB–Irradiated Hairless Mouse. J. Invest. Dermatol., 1988, pp. 175–180.

1990 Ed. Physicians' Desk Reference, Retin–A entry, p. 1570.

Mayumi et al. Pharmaceutical Intervention for the Prevention of Post–Ischemic Reperfusion Injury. Free Radicals: From Basic Science to Medicine. 1993, pp. 438–457.

Shields et al. Neutrophil Activation in Experimental Venous Hypertension. Phlebology (1994) 9:119–124.

Hung et al. Topical Tretinoin and Epithelial Wound Healing.

USE OF SUBSTITUTED (5,6) DIHYDRONAPHTHALENYL COMPOUNDS HAVING RETINOID-LIKE ACTIVITY TO PREVENT OR REDUCE ISCHEMIC INJURY

This application claims the benefit of U.S. Provisional Application No. 60/038,302, filed on Feb. 21, 1997.

The present invention provides methods for preventing or educing the severity of an ischemic injury to an animal's dermal tissue, using compounds having retinoid-like activity, namely, substituted (5,6)-dihydronaphthalenyl compounds. According to the present invention, substituted (5,6)-dihydronaphthalenyl compounds can be used to prevent or reduce the damage that occurs to dermal tissue when blood flow to the tissue is blocked, which can lead to ischemic injury.

The present application is related to U.S. application Ser. No. 08/464,186, filed Jun. 5, 1995, which is a continuation-in-part of U.S. application Ser. No. 08/306,092, filed Sep. 19, 1994, which is a continuation-in-part of U.S. application Ser. No. 08/216,740, filed Mar. 23, 1994, now abandoned, which in turn is a continuation-in-part of U.S. application Ser. No. 08/176,746, filed Jan. 3, 1994, now abandoned. These applications are hereby incorporated by reference into the present application in their entirety.

Patients who are comatose, diabetic, paraplegic or otherwise suffering from serious impairment of the neural and vascular systems are at greater risk of developing ischemic injury, such as pressure sores or ischemic ulcers. Such wounds tend to occur at parts of the body which are under compression such as the heels, elbows, hips, back and buttock.

A number of risk factors have been compiled which correlate with ischemic injuries. The four major risk factors in the occurrence of ischemic injuries are (1) pressure, (2) shear forces, (3) friction and (4) moisture. Additional predisposing risk factors include incontinence, fecal contamination, acid buildup, poor nutrition, advanced age, reduced mobility and poor physical condition.

Sustained pressure over a bony prominence leads to a high likelihood of ischemic injury with resulting tissue necrosis. Pressure induced ischemia of short duration is followed by a reactive hyperemia (reperfusion). After prolonged exposure to ischemia/reperfusion events, plasma leaks from vessels into interstitial tissues. Hemorrhage can occur and lead to non-blanching erythema. The accumulation of toxic metabolites and the lack of nutrients resulting from the occlusion of blood vessels and lymphatic channels lead to necrosis of muscle, subcutaneous tissues, and ultimately, the dermis and epidermis.

Shearing forces result from the sliding of a bony prominence against subcutaneous tissue, for example. Such sliding can occur, for example, when a patient is not completely lifted off a stationary surface such as a bed when the patient moves or is moved. The effects of both pressure and shearing forces generally begin in deeper tissues and eventually spread to the skin's surface. Frictional forces are generated, for example, from pulling a patient across a bed sheet. Friction may cause injuries such as intraepidermal blisters and ultimately superficial erosions. Moisture can increase the friction between two surfaces and can also lead to maceration. Frictional forces and moisture can lead to directly to the erosion of the superficial skin.

Combinations of any of the four major risk factors can result in more severe injury. Studies show that pressure-induced ischemia, followed by reperfusion, is the mechanism behind tissue necrosis. Thus, ischemic injury includes the damage caused by reperfusion, such as neutrophil mediated injury.

Ischemic injuries can also develop from other conditions that cause a shutoff or decrease of circulation to an area of dermal tissue, including blunt force trauma. In addition, ischemic injuries can result from skin stripping (removal of the outer epidermal layer) caused by the removal of pressure sensitive adhesives. For example, ostomates use collection devices having a pressure sensitive adhesive coated faceplate for attachment to the body around their surgically created stoma. Such devices are removed daily and in some instances, several times a day, for disposal. This constant peeling of adhesive can result in removal or stripping of the epidermal layer.

Ischemic injuries are a major source of patient discomfort and of medical expense, and the present invention provides methods for preventing or reducing the severity of ischemic injury using certain compounds having retinoid-like activity, such as binding to retinoic acid receptors.

SUMMARY OF THE INVENTION

The present invention relates to methods of preventing or reducing the severity of an ischemic injury to an animal's dermal tissue comprising administering to the animal a composition comprising a compound of formula I*:

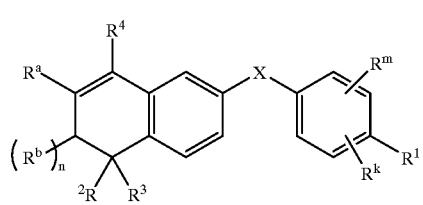

or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —CH=CH—, —C≡C—, —CH$_2$—NH—, —COCH$_2$—, —NHCS—, —CH$_2$S—, —CH$_{2O}$—, —OCH$_2$—, —NHCH$_2$— or —CR$^5$=CR$^6$—;

n is 1 or 0;

$R^m$ and $R^k$ are independently hydrogen, halogen, $C_{1-6}$ alkyl, hydroxy, $C_{1-6}$ alkyloxy or nitro;

$R^4$ is —(CH$_2$)$_t$—Y$^b$, $C_{1-6}$ alkyl, or $C_{3-6}$ cycloalkyl;

$R^1$ is —CO$_2$Z, $C_{1-6}$ alkyl, CH$_2$OH, —CONHR$^y$, or CHO;

$R^a$ and $R^b$ are independently hydrogen or $C_{1-6}$ alkyl, or $R^a$ and $R^b$ together can form a radical of the formula:

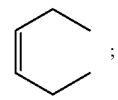

$Y^b$ is naphthyl or phenyl, both radicals can be optionally substituted with one to three of $C_{1-6}$ alkyl or halogen, which substituents can be the same or different;

Z is hydrogen or $C_{1-6}$ alkyl;

$R^2$, $R^3$, $R^5$, $R^6$, and $R^y$ are independently hydrogen or $C_{1-6}$ alkyl; and t is zero to six.

Preferably, $R^1$ is —CO$_2$H; n is one; $R^2$ and $R^3$ are independently methyl or hydrogen; and $R^a$ and $R^b$ are independently hydrogen or $C_{1-6}$ alkyl. Further, preferably $R^m$ and $R^k$ are hydrogen; $R^2$ is methyl; $R^3$ is methyl; $R^a$ and $R^b$ are hydrogen; X is —CH=CH—; $R^1$ is $CO_2Z$; and Z is hydrogen. In still further preferred embodiments, the compound is a compound of formula $I^{11}$ below in which $R^4$ is $(CH_2)_t$—$Y^b$, $C_{1-6}$ alkyl, or $C_{3-6}$ cycloalkyl, and most preferably the compound is 4-[[(E)-(5,6,-dihydro-5,5-dimethyl-8-phenyl)-2-naphthalenyl]vinyl]benzoic acid.

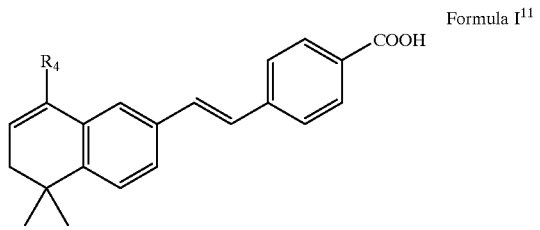

Formula $I^{11}$

In preferred methods of the invention, the composition is applied to a surface area of dermal tissue using a medicant bandage or dressing having a skin contacting adhesive surface. For example, the compound can be incorporated within an adhesive layer, coated onto a skin contacting adhesive surface or located at a skin contacting adhesive surface and adjacent strata of a bandage or dressing. In certain preferred embodiments, the dressing comprises a hydrocolloid adhesive.

Preferably, the compound is present in a topically applied the composition at about 0.01 % to about 1 % by weight of the composition. When the compound is applied in a bandage or dressing, preferably the compound is present at about 0.5 to about 1.0 mg/in² of the skin contacting adhesive surface of the bandage or dressing.

Preferably the compound is administered prior to the development of visually discernible damage to the dermal tissue.

In certain embodiments, the methods of the invention are used to prevent or reduce the damaging effects of an ischemic injury resulting from removal of an adhesive from the animal. In other embodiments, for example, the composition is administered to prevent or reduce the damaging effects of an ischemic injury resulting from pressure on dermal tissue covering a bony protuberance.

The reduction or prevention of injury using the methods of the present invention can be determined, for example, by measuring microcirculatory blood flow or by histological examination of a dermal tissue sample.

DETAILED DESCRIPTION OF THE INVENTION

The present invention relates to methods of preventing or reducing the severity of an ischemic injury to an animal's dermal tissue comprising administering a composition comprising a compound of formula I (shown above) or a nontoxic pharmaceutically acceptable salt, physiologically hydrolyzable ester or solvate thereof, with the substituents as described above. As alluded to above, those of ordinary skill will recognize a number of circumstances where the prophylactic administration of the invention can be applied to prevent or reduce the severity of tissue damage due to ischemic injury. For instance, in a hospital or nursing home setting, a patient who has to spend much of his or her time in bed will be at risk, particularly at the locations of bony protuberances. Patients who must repeatedly remove adhesive dressings are also at risk. Based on intensive studies undertaken to identify risk factors in order to diminish the high fiscal and quality of life costs of these injuries, significant guidance on when to intervene to reduce this risk is now available.

"Dermal tissue" is defined herein as tissue in any layer of the skin, including the epidermis, dermis and hypodermis. Injury to the dermal tissue includes injury originating in the dermal tissue that may optionally extend to other areas, including for example, muscle.

Preferred embodiments of the methods of the present invention include the use of compounds of the following formulas which are compounds of Formula I*, with the variable substituents being the same as defined for Formula I* above.

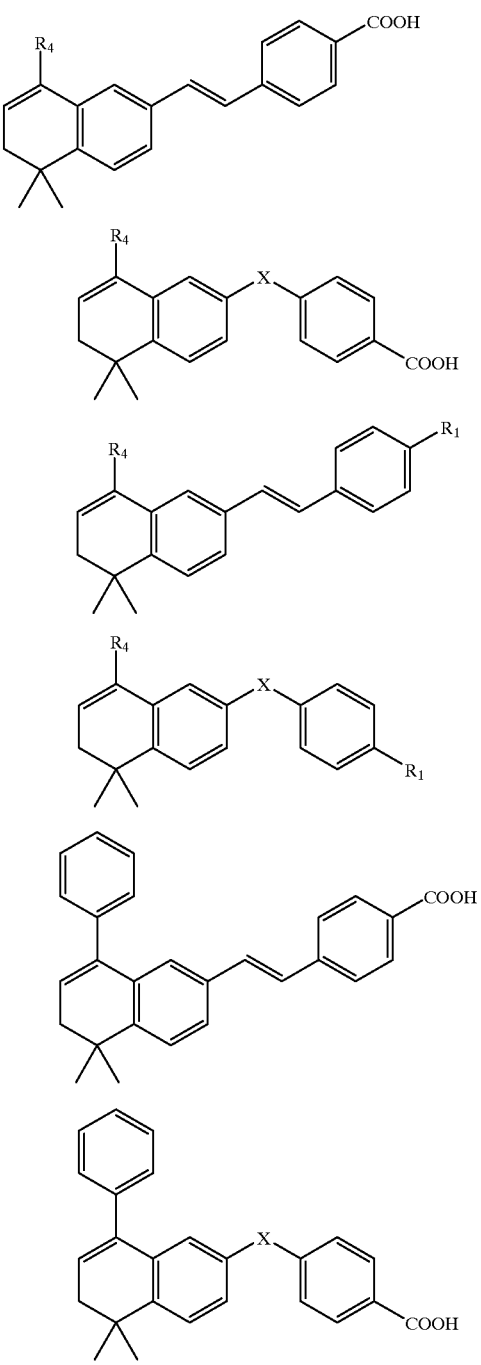

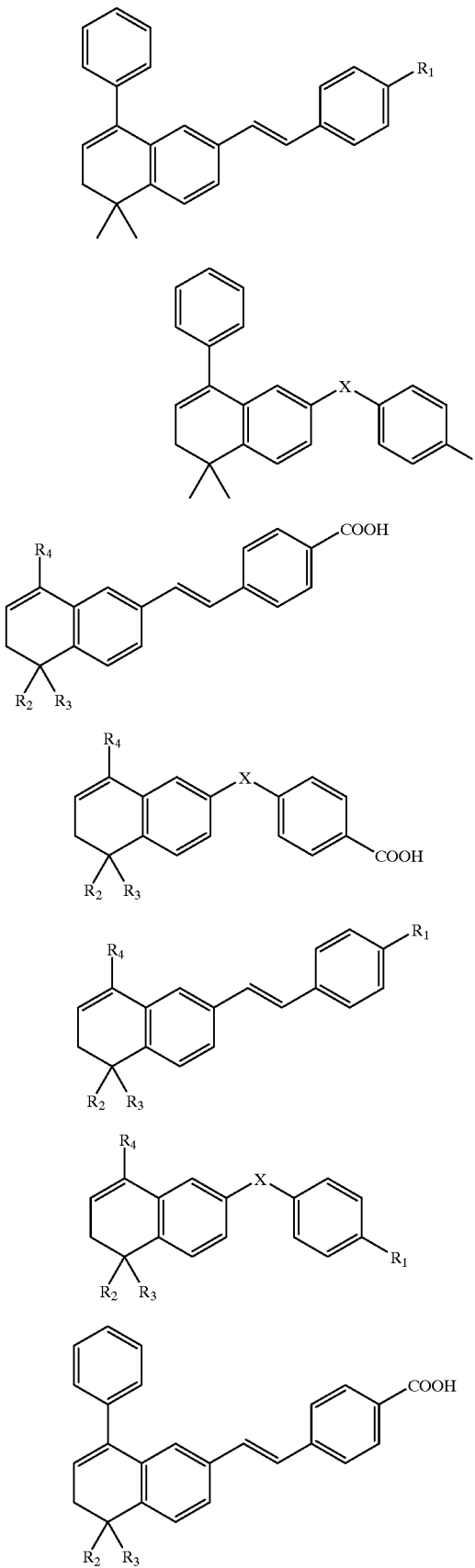
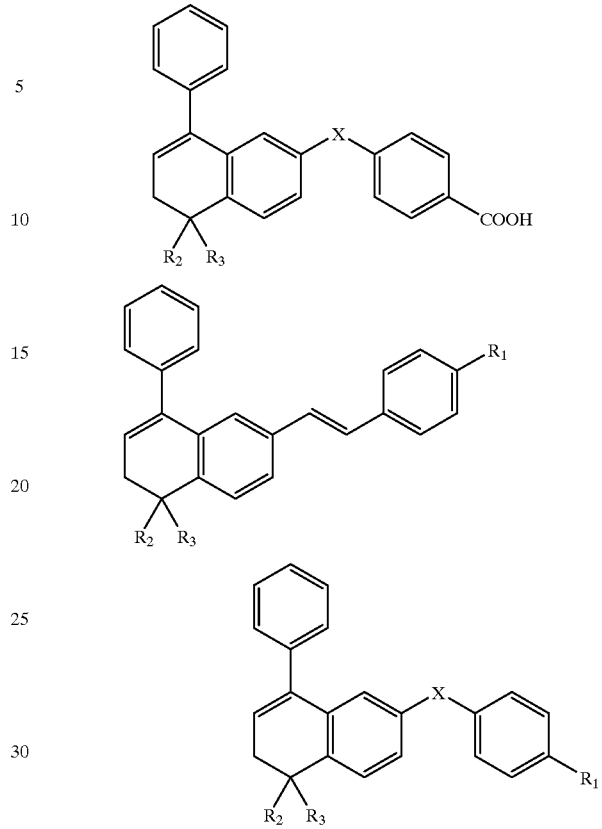

For the description herein, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{3-6}$ cycloalkyl refers to cyclopropyl, cylcobutyl, cyclopentyl, or cyclohexyl; and halogen refers to fluorine, chlorine, bromine, or iodine. In the instant application all symbols once defined retain the same meaning until they are redefined.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, ephenamine, N,N'-dibenzylethylenediamine, dehydroabietylamine, N-ethylpiperidine, benzylamine, dicyclohexylamine, or the like pharmaceutically acceptable amines.

When a compound of formula I contains carboxy groups, it can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, benzyl, 4-methoxybenzyl, indanyl, phthalidyl, methoxymethyl; $C_{1-6}$ alkanoyloxy $C_{1-6}$ alkyl, e.g. acetoxymethyl, pivaloyloxymethyl or propionyloxymethyl; $C_{1-6}$ alkoxycarbonyloxy $C_{1-6}$ alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephalosporin arts. Such esters are prepared by conventional techniques known in the art.

The structural formulae as drawn in the instant application are believed to best represent the structures of compounds used in the methods of the present invention. However, some compounds for use within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods using conventional starting materials and processes. See, for example, EP 0 661 259 A1, which is hereby incorporated by reference herein in its entirety, and U.S. application Ser. No. 08/464,186, filed June 5, 1995.

Examples of chemical formulas encompassed by formula I* include:

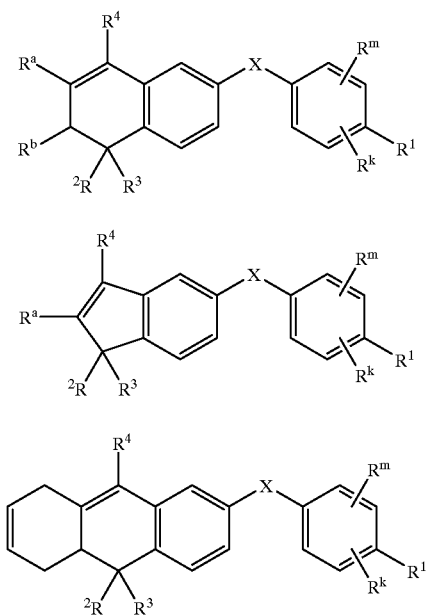

In the above formula D, n is equal to one, while in formula E, n is equal to zero. In formula F, $R^a$ and $R^b$ together form a fused ring structure.

The compounds of formula I may be used topically or systemically, in the treatment, amelioration, or prevention of ischemic injury or reperfusion. In this regard, they may be used for therapy in animals, including humans, for prophylaxis or treatment. When used for treatment, they will usually be formulated with a pharmaceutically acceptable liquid, semi-solid, or solid carrier. A pharmaceutically acceptable carrier is a material that is nontoxic and generally inert and does not affect the functioning of the active ingredients adversely.

Such materials are well known and include those materials sometimes referred to as diluents or vehicles (excipients) in the pharmaceutical formulation art. The carrier may be organic or inorganic in nature.

Examples of pharmaceutically acceptable carriers that may be used to formulate a compound of formula I include water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated or prevented and particulars of the patient being treated. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. Accordingly, optimal therapeutic concentrations will be best determined at the time and place through routine experimentation.

In many embodiments it is preferred to administer the drug topically, and in other embodiments, oral administration is a preferred means of administration. If the compounds according to the invention are used topically, it will be found that they exhibit a good activity over a very broad range of dilution. For example, preferred compositions for topical application have a concentration of the active compound or compounds from about 0.0005% wt/vol to about 10% wt/vol, more preferably from about 0.01% to about 1%, yet more preferably from about 0.05% to about 0.5%, still more preferably about 0.1%. Dosages for systemic administrations are preferably designed to administer from about 0.5 to about 50 mg/kg/day of the active compound or compounds, and more preferably, about 10 mg/kg.

For topical administration the compounds of formula I are conveniently provided in the form of unguents, gels, creams, ointments, powders, dyeing compositions, solutions, suspensions, emulsions, lotions, sprays, adhesive plasters and impregnated pads. The compounds according to the invention can be mixed with inert nontoxic, generally liquid or pasty, materials suitable for topical treatment.

Preparation of such topical formulations are well described in the art of pharmaceutical formulations as exemplified, for example, Remington's Pharmaceutical Science, (17th ed., Mack Publishing Company, Easton, Pa.). Other medicaments can be added to such topical formulation for such secondary purposes as treating skin dryness, providing protection against light; other medications for treating dermatoses, preventing infection, reducing irritation, inflammation and the like.

The active compounds can also be administered enterally. For oral administration, suitable forms are, for example, tablets, pills, dragees, syrups, suspensions, emulsions, solutions, powders and granules; a preferred method of administration consists in using pills.

U.S. Pat. No. 4,876,381 issued on Oct. 24, 1989 to Lang et al. provides examples of formulations constituting gel, unguent, powder, cream, etc. for a retinoid compound. The aforesaid U.S. Patent can be used as a guide to formulate a compound of formula I and is herein incorporated by reference in its entirety.

The compounds according to the invention can also be administered parenterally in the form of solutions or suspensions for intravenous or intramuscular perfusions or injections. A preferred method of administration consists of using solutions or suspensions containing approximately from 0.01 mg to 1 mg of active substance per ml.

The present invention is most promising for application in humans, where the detrimental effects of ulcers caused by ischemic injury understandably command greater attention. However, situations also arise that are likely to cause such injury in animals. The preferred treatment subjects are mammals, particularly humans.

Experiments have shown that compounds of formula 1 are at least antagonists of retinoic acid in some systems, such as induced activation of transcription mediated by the alpha, beta and gamma retinoic acid receptors. These compounds also show some agonist activity.

The invention is further described by the following non-limiting example.

EXAMPLE 1
Prevention of Ischemic Injury

Male Hartley guinea pigs weighing 350–400 grams were individually housed and fed a basal diet of feed, and water ad libitum. The guinea pigs were housed in a controlled environment with a temperature ranging from 19–21 degrees Celsius, a twelve hour light/dark cycle, and 50% relative humidity.

Twenty-five guinea pigs were zip wax depilated four days prior to the start of the experiment. The guinea pigs were randomly divided into five treatment groups, with five guinea pigs in each group. Group 1 was treated with 0.01% wt/vol 4-[[(E)-(5,6-Dihydro-5,5-dimethyl-8-phenyl)-2-naphthalenyl]vinyl]benzoic acid in ethanol ("0.01% B.A."). 4-[[(E)-(5,6-Dihydro-5,5-dimethyl-8-phenyl)-2-naphthalenyl]vinyl]benzoic acid ("B.A.")has the following structure:

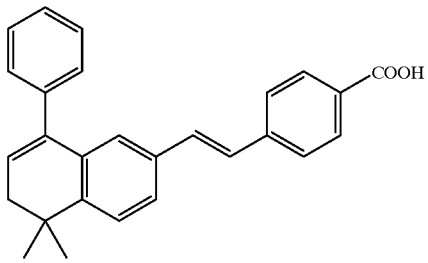

Group 2 was treated with 0.1% B.A. in ethanol. Group 3 was treated with 0.1% all-trans retinoic acid in 100% ethanol ("0.1% RA."). Group 4 was a control group treated with ethanol before and after ischemic injury was surgically induced. Group 5 was treated with 0.1% B.A. in ethanol both before and after ischemic injury was surgically induced.

100 microliters of each treatment solution was applied to each of the guinea pigs in the treatment group by contacting a 10 cm² area of skin with a micropipette containing the treatment solution. The site of treatment was then occluded with Tegaderm brand transparent film dressing (Minnesota Mining and Manufacturing, St. Paul, Minn.). The treatment was repeated for a total of four consecutive days, with one treatment per day. A fifth application of each treatment solution was applied to each guinea pig in a group after the surgery described below.

See Table I below.

TABLE 1

| Group Number | Treatment Solution | Pre-treatment | Induction of Ischemia | Post-treatment |
| --- | --- | --- | --- | --- |
| 1 | 0.01% B.A. | Days 1–4 | Day 5 | None |
| 2 | 0.1% B.A. | Days 1–4 | Day 5 | None |
| 3 | 0.1% R.A. | Days 1–4 | Day 5 | None |
| 4 | Ethanol | Days 1–4 | Day 5 | Post-Ischemia Days 1, 3, 7 & 10 |
| 5 | 0.1% B.A. | Days 1–4 | Day 5 | Post-Ischemia Days 1, 3, 7 & 10 |

Ischemic ulcers were induced on the guinea pigs as follows. The entire dorsal region of each guinea pig was prepared for surgery by washing the skin with antiseptic scrub, followed by a warm water rinse.

The guinea pigs were anesthetized by an intraperitoneal injection of 100 mg/kg Ketamine (Ketaset™, Bristol-Myers Squib, Princeton, N.J.) followed by an intramuscular injection of 0.6 ml Xylazine (Rompun™, Bayer AG, Leverkusen, Germany) at a concentration of 5 mg/kg. The combination provided about 45 minutes of surgical anesthesia, during which time surgery was performed.

A five cm transcapular incision was made with a no. 10 scalpel blade. The skin was carefully undermined using blunt dissection until a narrow pocket was formed to accommodate a sterile 10 ml rubber syringe plunger. A concerted effort was made to minimize damage to the underlying tissue and focus only on the vertebral region where the plunger was placed. The rubber plunger was inserted over the vertebral region distant to the scapula. An orthodontic rubber band tourniquet was placed around the plunger to prevent blood flow to the five square cm of skin above the rubber plunger. The incision line was closed with wound staples (Ethicon, Somerville, N.J., a subsidiary of Johnson & Johnson Products).

The rubber plunger was left in the incision for six hours after surgery. After this six hour period, the guinea pigs were anesthetized again using an intraperitoneal injection of Ketamine HCl. The incision was reopened, the rubber band was released, and the rubber plunger was removed by pulling an exposed suture attached to the rubber tip.

Following release of the tourniquet, a fifth application of each treatment solution was applied to the surgical site on each guinea pig in a group. The site was then occluded with Tegaderm brand dressing secured to the skin using elastic tape.

The guinea pigs in Groups 4 and 5 were further treated on the first, third, seventh and tenth days after surgery using the relevant treatment solution.

On the first, third, seventh, and tenth days after surgery, all of the guinea pigs were visually checked for tissue necrosis, which was subsequently recorded as a percentage of full thickness damage, superficial damage, or viable tissue. Full-thickness damage was defined as involving both the epidermis and the dermis, extending down to muscle. Superficial damage was defined as involving the epidermis and part of the dermis. Viable tissue was defined as pink, blanchable skin.

Photographs were taken throughout the study. The guinea pigs were then euthanized.

On day ten, skin samples, including the epidermis, dermis and hypodermis, were taken from the adjacent and opposing sites in the ischemic area for histological evaluation. The skin samples were then fixed in 10% buffered formalin and processed for light microscopic evaluation. Hematoxylin-eosin and Masson's trichrome-stained sections were prepared for histological evaluation which was carried out by a person without prior knowledge of the kind of treatment received by each guinea pig. The histological evaluation of the skin included a rating as normal, mild, moderate or marked changes. The epidermis was evaluated for vacuolation of cells, mitosis, inflammation and necrosis. The dermis was evaluated for neovascularization, inflammation and necrosis. The hypodermis was evaluated for the presence of granulation tissue, inflammation, angiogenesis and blood cell extravasation. Changes in the collagen matrix or cellular morphology were also noted.

In response to the ischemic injury and the treatments, a range of visual evaluations and histological evaluations were found. Variations in response within a treatment group was not specific to a particular group.

Visual Assessment of Skin Damage

Group 1: animals treated with 0.01% 4-[[(E)-(5,6-Dihydro-5,5-dimethyl-8-phenyl)-2-naphthalenyl]vinyl] benzoic acid. Three guinea pigs were observed, the other two having expired under anesthesia. One had normal intact skin, while the other two showed full-thickness necrosis with sparse areas of viable tissue.

Group 2: animals treated with 0.1% 4-[[(E)-(5,6-Dihydro-5,5-dimethyl-8-phenyl)-2-naphthalenyl]vinyl]benzoic acid. The guinea pigs in this group showed a marked reduction in dermal tissue breakdown when compared to the other groups.

Group 3: animals treated with 0.1% all-trans retinoic acid. Full-thickness damage was prevented, and more superficial damage was observed on days 7 and 10.

Group 4: animals treated with 100% ethanol control (before and after surgically induced injury). This group appeared to have the most extensive and highest degree of full-thickness damage.

Group 5: animals treated with 0.1% 4-[[(E)-(5,6-Dihydro-5,5-dimethyl-8-phenyl)-2-naphthalenyl]vinyl]benzoic acid both before and after surgically induced injury. The incidence and severity of necrosis varied in this group.

The data for the visual skin assessment is summarized in Tables 2 and 3. Table 2 is a compilation of data for the seventh day after ischemia was induced, and Table 3 is a compilation of data for the tenth day after ischemia was induced.

TABLE 2

Results after 7 days

| Treatment Group | Treatment Solution | % Full-Thickness Damage | % Superficial Damage | % Viable Tissue |
|---|---|---|---|---|
| 1 | 0.01% B.A. | 64% | 0% | 36% |
| 2 | 0.1% B.A. | 0% | 20% | 80% |
| 3 | 0.1% R.A. | 0% | 100% | 0% |
| 4 | Ethanol | 82% | 16% | 2% |
| 5 | 0.1% B.A. pre- and post-ischemia | 20% | 25% | 55% |

TABLE 3

Results after 10 days

| Treatment Group | Treatment Solution | % Full-Thickness Damage | % Superficial Damage | % Viable Tissue |
|---|---|---|---|---|
| 1 | 0.01% B.A. | 64% | 0% | 36% |
| 2 | 0.1% B.A. | 0% | 10% | 90% |
| 3 | 0.1% R.A. | 0% | 70% | 30% |
| 4 | Ethanol | 80% | 5% | 15% |
| 5 | 0.1% B.A. pre- and post-ischemia | 20% | 20% | 60% |

The results with group 5, where the agent in vehicle was administered both before and after ischemia was induced, are intermediate between those for 2 and group 4, consistent with the known deleterious effect of the vehicle, ethanol, on wound healing.

Histological Findings

Group 1: animals treated with 0.01% 4-[[(E)-(5,6-Dihydro-5,5-dimethyl-8-phenyl)-2-naphthalenyl]vinyl] benzoic acid. Skin reactions from three treated guinea pigs were submitted for microscopic examination. The skin of one guinea pig appeared quite normal and intact. The other two guinea pigs revealed profoundly affected skin. Their epidermis was markedly eroded and in some areas, particularly at the site of ischemia, it was missing. At this site, the hair follicles were eradicated. An intense inflammatory reaction consisting mostly of macrophages, mast cells, histocytes and persistent eosinophils were seen in the papillary dermis just beyond the eroded stratum corneum as well as in the lower region of the reticular dermis and the hypodermis. Massive extravasation of blood cells was noted in the reticular dermis and discrete hemorrhages were common. Distorted, disrupted and hyalinized collagen fibers appeared mostly in the reticular dermis close to the hypodermis. Moderate fibroplasia appeared confined to the hypodermis.

Group 2: animals treated with 0.1% 4-[[(E)-(5,6-Dihydro-5,5-dimethyl-8-phenyl)-2-naphthalenyl]vinyl]benzoic acid. Skin sections from four animals were available for histological evaluation. One guinea pig showed intact and normal epidermis and dermis mildly invaded by inflammatory cellular infiltrates. The other three guinea pigs, despite showing eroded stratum corneum, manifested a mild inflammatory reaction in both the dermis and the hypodermis. The dermal collagen appeared mostly normal. The hypodermis showed very mild to moderate fibroplasia.

Group 3: animals treated with 0.1% all-trans retinoic acid. The skin of four out of the five guinea pigs manifested a mild to moderate inflammatory reaction in both of the papillary and reticular regions of the dermis. However, the collagen fibers showed more damage in the lower region of the dermis than in the upper one. The hypodermis showed normal and intact muscle fibers. One guinea pig responded differently to the treatment, and intense inflammatory cellular infiltrates and particularly massive populations of eosinophils were observed invading all the regions of the skin.

Group 4: animals treated with 100% ethanol control (before and after surgically induced injury). This group, as a whole, manifested the most profound changes in the skin. A severe inflammatory reaction prevailed in the epidermis, dermis and in the hypodermis. The inflammatory cellular infiltrates contained neutrophils, macrophages and a massive population of eosinophils. As a result of this excessive inflammatory reaction, the collagen fibers in the dermis appeared to be disrupted and hyalinized. Hemorrhagic areas were frequently encountered particularly in the lower region of the hypodermis.

Group 5: animals treated with 0.1% 4-[[(E)-(5,6-Dihydro-5,5-dimethyl-8-phenyl)-2-naphthalenyl]vinyl]benzoic acid (before and after surgically induced injury). The guinea pigs in this group showed a varied response to the treatment. Two out of the five guinea pigs showed an insignificant reaction while the others showed moderate to severe changes. One guinea pig manifested a severe inflammatory reaction involving all regions of the skin. Macrophages, neutrophils and massive populations of eosinophils were the main constituents of the inflammatory cellular infiltrates. Most of the collagen fibers were disintegrated, hyalinized and some already disappeared. The muscle fibers in the hypodermis were drastically affected and appeared worn out and many were sacrolyzed.

Overall, the test results showed that pre-treatment of guinea pigs with 0.1% 4-[[(E)-(5,6-Dihydro-5,5-dimethyl-8-phenyl)-2-naphthalenyl]vinyl]benzoic acid before surgically induced injury reduced the incidence and severity of inflammation, damage to collagen fibers and overall dermal necrosis. The guinea pigs in this treatment group showed acceleration and amelioration in the repair of ischemic site superior to the other treatment groups.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of preventing or reducing the severity of an ischemic injury originating in an animal's dermal tissue comprising administering to the animal a composition comprising a compound of formula I*:

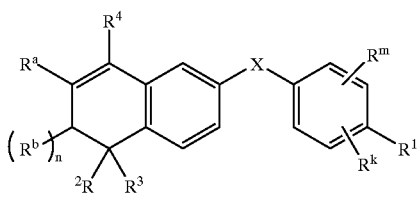

or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$═CR$^6$—;

n is 1 or 0;

R$^m$ and R$^k$ are independently hydrogen, halogen, C$_{1-6}$ alkyl, hydroxy, C$_{1-6}$ alkyloxy or nitro;

R$^4$ is —(CH$_2$)$_t$—Y$^b$, C$_{1-6}$ alkyl, or C$_{3-6}$ cycloalkyl;

R$^1$ is —CO$_2$Z, C$_{1-6}$ alkyl, CH$_2$OH, -CONHR$^y$, or CHO;

R$^a$ and R$^b$ are independently hydrogen or C$_{1-6}$ alkyl, or R$^a$ and R$^b$ together can form a radical of the formula:

Y$^b$ is naphthyl or phenyl, both radicals can be optionally substituted with one to three of C$_{1-6}$ alkyl or halogen, which substituents can be the same or different;

Z is hydrogen or C$_{1-6}$ alkyl;

R$^2$, R$^3$, R$^5$, R$^6$, and R$^y$ are independently hydrogen or C$_{1-6}$ alkyl; and t is zero to six.

2. The method of claim 1, in which R$^1$ is —CO$_2$H; n is one; R$^2$ and R$^3$ are independently methyl or hydrogen; and R$^a$ and R$^b$ are independently hydrogen or C$_{1-6}$alkyl.

3. The method of claim 1, in which the compound is 4-[[(E)-(5,6,-dihydro-5,5-dimethyl-8-phenyl)-2-naphthalenyl]vinyl]benzoic acid.

4. The method of claim 1, in which R$^2$ is methyl.

5. The method of claim 4, in which R$^3$ is methyl.

6. The method of claim 1, in which R$^m$ and R$^k$ are hydrogen.

7. The method of claim 1, in which R$^a$ and R$^b$ are hydrogen.

8. The method of claim 1, in which X is —CH═CH—.

9. The method of claim 1, in which R$^1$ is CO$_2$Z.

10. The method of claim 9, in which Z is hydrogen.

11. The method of claim 1, wherein the composition comprises a compound of formula I$^{11}$:

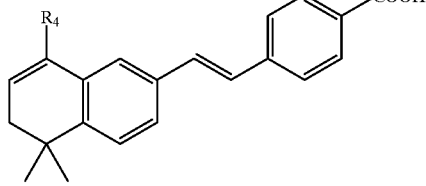

in which R$^4$ is —(CH$_2$)$_t$—Y$^b$, C$_{1-6}$alkyl, or C$_{3-6}$cycloalkyl.

12. The method of claim 1, wherein the composition is administered in a medicant bandage or dressing having an adhesive layer or surface for adhering to the animal's skin.

13. The method of claim 12, wherein the compound is incorporated within an adhesive layer or is coated onto an adhesive surface or is located at an adhesive surface and adjacent strata of a bandage or dressing.

14. The method of claim 12, wherein the dressing comprises a hydrocolloid adhesive.

15. The method of claim 12, wherein the compound is present at about 0.5 to about 1.0 mg/in$^2$ of the skin contacting adhesive surface of the bandage or dressing.

16. The method of claim 12, wherein the medicant bandage or dressing is applied prior to the development of visually discernible damage to dermal tissue.

17. The method of claim 1, wherein the compound is present in a topical composition at about 0.01% to about 1% by weight of the composition.

18. The method of claim 1, wherein the reduction or prevention of injury is determined by measuring microcirculatory blood flow.

19. The method of claim 1, wherein the reduction or prevention of injury is determined by histological examination of a dermal tissue sample.

20. The method of claim 1, wherein the composition is applied to prevent or reduce the damaging effects of an ischemic injury resulting from removal of an adhesive from the animal.

21. The method of claim 1, wherein the composition is applied to prevent or reduce the damaging effects of an ischemic injury resulting from pressure on dermal tissue covering a bony protuberance.

* * * * *